United States Patent [19]

Grooters

[11] Patent Number: 5,131,905
[45] Date of Patent: Jul. 21, 1992

[54] EXTERNAL CARDIAC ASSIST DEVICE

[76] Inventor: Ronald K. Grooters, 3300 Fuller Rd., West Des moines, Iowa 50265

[21] Appl. No.: 552,589

[22] Filed: Jul. 16, 1990

[51] Int. Cl.$^5$ ............................................ A61N 1/362
[52] U.S. Cl. ........................................ 600/16; 623/3; 128/64
[58] Field of Search ................................ 600/16–18; 623/3; 128/24.2, 44, 64, 158–162

[56] References Cited

U.S. PATENT DOCUMENTS

| | | | |
|---|---|---|---|
| 3,455,298 | 7/1969 | Anstadt | 128/64 |
| 4,192,293 | 3/1980 | Asrican | 600/17 |
| 4,213,207 | 7/1980 | Wilson | 128/417 |
| 4,536,893 | 8/1985 | Parravicini | 623/3 |
| 4,599,083 | 7/1986 | Perlov . | |
| 4,621,617 | 11/1986 | Sharma | 600/16 |
| 4,690,134 | 9/1987 | Snyders | 128/44 |

FOREIGN PATENT DOCUMENTS

| | | | |
|---|---|---|---|
| 2527435A | 12/1983 | France | 600/16 |
| 247015A | 11/1987 | Sweden | 600/16 |

OTHER PUBLICATIONS

Hekmatpanah; "Value of Mechanical Ventricular Assistance . . . ", *Journal of Surgical Research*; vol. 18, pp. 539-544 (1975).

Anstadt, "Prolonged Circulatory Support by Direct Mechanical Ventricular Assistance", *Trans. Amer. Soc. Artif. Int. Organs*; vol. XII; pp. 72-79; (1966).

Kantrowitz, "A Chronical of Main Currents in Left Ventricular Assistance", *Artificial Organs–International Society for Artificial Organs*, 10(5): 364–369.

Anstadt, "Prolonged Cirulatory Support by Direct Mechanical Ventricular Assistance for Two to Three Days . . . ", *Trans Amer. Soc. Artif. Int. Organs*; vol. XVII; pp. 174-182 (1971).

Baue, "Mechanical Ventricular Assistance in Man"; *Supplement II to Circulation*, vols. XXXVII and XXXVIII, pp. 11-33-11-36, Apr. (1968).

Anstadt, "Continued Studies in Prolonged Circulatory Support by Direct Mechanical Ventricular Assistance", *Trans. Amer. Soc. Artif. Int. Organs*, vol. XIV; pp. 297-303 (1968).

Hoffer, "Mechanical Ventricular Assistance for Circulatory Support in Acute Coronary Artery Occusion in the Pig: The Anstadt Cup"; *Diseases of the Chest*, vol. 53(4), pp. 502-506; Apr. (1968).

Anstadt, "Mechanical Ventricular Assistance for Prolonged Support of the Heart"; *Surgical Forum*, 52nd Ann. Clinic Cong.; pp. 148-149 (1966).

Skinner, "Mechanical Ventricular Assistance in Human Beings"; *The Annals of Thoracic Surgery*; vol. 5, No. 2; pp. 131-140; Feb. (1968).

*Primary Examiner*—William E. Kamm
*Assistant Examiner*—J. P. Lacyk
*Attorney, Agent, or Firm*—Zarley, McKee, Thomte, Voorhees & Sease

[57] ABSTRACT

An external cardiac assistance device is provided for augmenting cardiac contractions. The device includes a flexible, non-distensible shell adapted to be positioned over the base of the heart. A distensible membrane is mounted within the shell to define an inflatable space so that the device can be used on various sized hearts. Inflatable compartments are formed within the shell adjacent the membrane so as to engage the left and right ventricles of the heart. The device can be manually held in position on the heart by a handle for short-term use, or by a plurality of straps for intermediate and long term use. The device is operatively connected to an EKG machine which actuates a fluid pump in response to the QRS waves of the heart so as to rhythmically inflate and deflate the compartments to assist with the contractions of the heart.

21 Claims, 2 Drawing Sheets

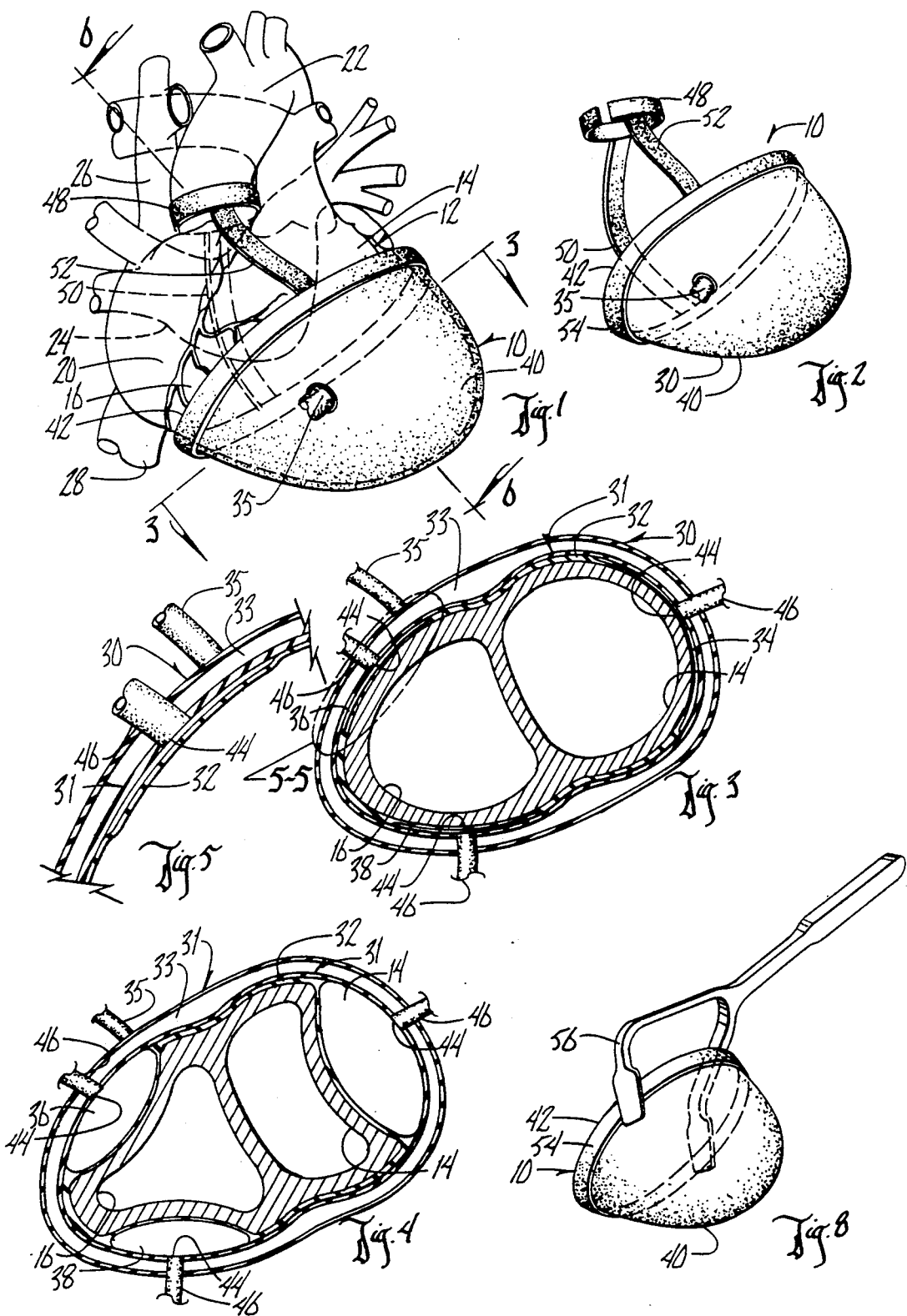

EXTERNAL CARDIAC ASSIST DEVICE

BACKGROUND OF THE INVENTION

Cardiac assist devices have been known and used for many years for assisting the contractions of a weak or diseased heart. For example, the Anstadt cup employs an outer glass housing with an inner diaphragm which is held onto the cardiac ventricles by suction. Alternating positive and negative pressures are delivered into the space between the cup and diaphragm to effect systolic contraction and diastolic relaxation. However, the suction required to hold the Anstadt cup in place can cause damage to the heart muscle.

U.S. Pat. No. 4,690,134 issued to Snyders also discloses an external ventricular assist device which utilizes inflatable chambers within a shell for supplementing cardiac output. The Snyders device is sutured to the pericardial sac. Thus, the Snyders device is not intended for short term use, such as to provide cardiac assist during surgery.

Internal cardiac assist devices are also known, but generally require the use of an anticoagulant to thin the blood, which leads to increased bleeding. Arterial balloon pumps also require an anticoagulant.

Therefore, a primary objective of the present invention is the provision of an improved external cardiac assist device.

Another objective of the present invention is the provision of a cardiac assist device which is useful for short term and long term applications.

A further objective of the present invention is the provision of a cardiac assist device which can be used during sudden decompensation of the heart, shortly after heart surgery to support low cardiac output, as a bridge to transplantation, and to permanently augment the heart.

Still another objective of the present invention is the provision of a cardiac assist device which eliminates the need for an anticoagulant, which eliminates neurological injury secondary to potential emboli, which eliminates the need for multiple cannulation techniques, and which reduces bleeding complications.

Still another objective of the present invention is the provision of a cardiac assist device which prevents cardiac rhythmic problems or fibrillation.

A further objective of the present invention is the provision of a cardiac assist device which utilizes chambers which can be adjustably inflated to provide varying degrees of cardiac assist and for various sized hearts.

An additional objective of the present invention is the provision of a cardiac assist device which can be fixed to the heart without the use of suction or sutures.

Another objective of the present invention is the provision of an external cardiac assist device which can be quickly and easily employed.

Another objective of the present invention is the provision of a cardiac assist device which is safe in use and medically acceptable.

These and other objectives will become apparent from the following description of the invention.

SUMMARY OF THE INVENTION

The external cardiac assist device of the present invention employs a heart bag which is secured to the heart with adjustable straps. For short term use or emergency use, the bag can be positioned on the heart with a disconnectable handle.

The device includes a flexible, non-distensible shell. A distensible inner membrane is secured along portions of the inner wall of the shell to define inflatable chambers. When the device is positioned over the base of the heart, one chamber engages the left ventricle while two other chambers engage opposite sides of the right ventricle. Each chamber is operatively connected to a fluid pump by fluid lines which allow fluid, either liquid or gas, to be rhythmically pumped into and out of the chambers to assist the systolic contractions of the heart. The device is operatively connected to an EKG machine which coordinates the pumping action in response to the QRS waves from the heart. The chambers are actively deflated shortly after inflation to allow the heart to fill and be ready for the next contraction.

BRIEF DESCRIPTION OF THE DRAWINGS

FIG. 1 is a perspective view of the cardiac assist device of the present invention as positioned on a heart.

FIG. 2 is a perspective view of the device, apart from the heart.

FIG. 3 is a sectional view taken along lines 3—3 of FIG. 1 with the compartments shown as deflated.

FIG. 4 if a view similar to FIG. 3, showing the compartments as inflated.

FIG. 5 is an enlarged view taken along lines 5—5 of FIG. 3.

FIG. 8 is a perspective view of the device shown with a removable handle for short term use of the device.

DETAILED DESCRIPTION OF THE INVENTION

Figure 6:
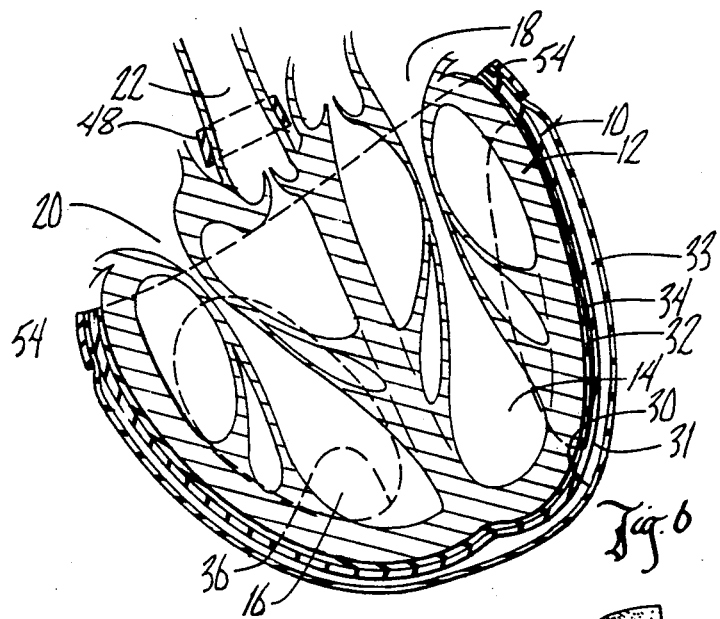
FIG. 6 is a sectional view taken along lines 6—6 of FIG. 1.

The cardiac assist device of the present invention is generally designated by the reference numeral 10 in the drawings, while the heart is designated by the reference numeral 12. The heart includes the left ventricle 14, the right ventricle 16, the left atrium 18 and right atrium 20. The aorta 22, the transverse sinus 24, the superior vena cava 26, and the inferior vena cave 28 are also shown in FIGS. 1 and 6.

As shown in FIGS. 3-5, the device, or heart bag, of the present invention includes an outer flexible, non-distensible shell 30 having opposite inner and outer walls, a first distensible membrane 31 and a second distensible inner lining or membrane 32 secured to the first membrane 31 along portions thereof. Membrane 31 is secured to shell 30 around the upper perimeter edge of the shell so as to define an inflatable space 33 which can be filled with a liquid or gas through a supply hose 35. Space 33 can be inflated such that membrane 32 completely engages the heart, thereby allowing device 10 to be used on various sized hearts. For example, on a large heart, space 33 is collapsed and on smaller hearts, space 33 is inflated accordingly.

Figure 7:
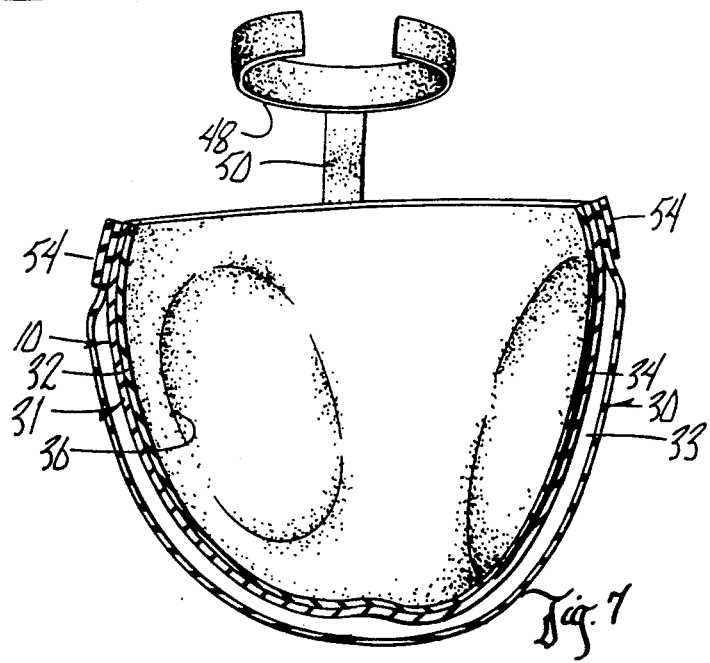
FIG. 7 is a view similar to FIG. 6 showing the device apart from the heart.

A plurality of chambers or compartments are formed between membrane 31 and inner membrane 32 where the membranes 31, 32 are not sealed to one another. More particularly, a first chamber 34 is formed on one side or end of device 10, while second and third chambers 36, 38 are formed in device 10 opposite chamber 34. As seen in FIG. 7, chamber 34 is elongated and extends substantially from the closed bottom end 40 of the device to the open upper end 42 of device 10. In comparison, chambers 36 and 38 are relatively smaller in dimension than chamber 34. The shape of chamber 34 accommodates the cone shape of the left ventricle, while the shape and location of chambers 36 and 38 accommodate the bellows shape of the right ventricle.

External communication is provided to each chamber 34, 36, 38 through an aperture 44. The chambers are operatively connected to a fluid source, such as a conventional balloon pump (not shown) by a fluid line 46 which is secured to each aperture 44 in any convenient manner.

Device 10 is positioned around the base of the heart such that chamber 34 engages left ventricle 14 and chambers 36 and 38 engage the opposite sides of right ventricle 16, as best seen in FIG. 4. Device 10 is secured to the heart for intermediate and long term cardiac assistance by means of a plurality of adjustable straps. More particularly, a first strap or band 48 is wrapped around the aorta 22, with the opposite ends of the strap being secured by any convenient means. A second strap 50 extends from the aorta strap 48 between the heart 12 and the transverse sinus 24, and behind the left atrium 18 and is connected to the upper end 42 of shell 30. An additional strap 52 may also be attached at one end to the aorta strap 48 and at the opposite end to the open upper end 42 of the shell 30, so as to extend in front of the right atrium 20. Also, a perimeter strap is attached to the upper end 42 of the shell so as to wrap around the base of the heart 12. Each of straps 48, 50, 52 and 54 are adjustable by any known manner so as to accommodate different sized hearts.

As an alternative to the straps, device 10 can be positioned temporarily on the heart, for example during surgery, by the use of a detachable handle 56, as seen in FIG. 8. The shape of a handle 56 is not critical and the attachment of the handle to the shell 30 is by any known means.

In use, device 10 is positioned on a weak or diseased heart to facilitate the systolic contractions of the heart. If device 10 is to be utilized for a period other than during surgery, straps 48, 50, 52 and 54 are secured around the aorta and the heart as described above. Fluid lines 46 are connected to apertures 44 and shell 30. Fluid lines 46 may be branched from a single fluid supply line (not shown) such that only one cannular is required. The heart 12 is operatively connected to an EKG machine (not shown) which senses the QRS waves of the heart to activate the pump for supplying fluid to compartments 34, 36 and 38 in timing with the contractions of the heart. The liquid or gas which fills the chambers is also actively suctioned from the chambers by the pump between heart contractions. The extent of inflation of the chambers can be controlled and adjusted so as to provide the necessary degree of assistance to the cardiac contractions.

From the foregoing, it can be seen that the present invention accomplishes at least all of the stated objectives.

What is claimed is:

1. A cardiac assist device for use externally on the heart, comprising:
    a single flexible, nondistensible shell adapted to be positioned over the base of the heart, and having inner and outer walls;
    a first inflatable compartment within the shell and adapted to engage the left ventricle;
    second and third inflatable compartments within the shell and adapted to engage the right ventricle on substantially opposite sides;
    means for positioning the shell on the heart; and
    means for rhythmically inflating and deflating the first, second and third compartments so as to assist the contraction of the heart.

2. The cardiac assist device of claim 1 further comprising a distensible membrane secured within the shell to define an inflatable space along the inner wall of the shell, and means for inflating the space.

3. The cardiac assist device of claim 1 wherein the means for positioning the shell includes a plurality of straps secured around the heart to prevent movement of the shell relative to the heart.

4. The cardiac assist device of claim 3 wherein the straps are adjustable.

5. The cardiac assist device of claim 1 wherein the means for positioning the shell includes a band adapted to be positioned around the aorta, and at least one strap extending from the band to the shell.

6. The cardiac assist device of claim 5 wherein the shell includes an open upper end with a perimeter edge, and the means for positioning the shell further comprising a second strap attached to and extending around the perimeter edge of the shell.

7. The cardiac assist device of claim 6 wherein the one strap and the second strap are adjustable.

8. The cardiac assist device of claim 1 wherein the first, second, and third compartments are spaced apart and extend only partially along the inner wall of the shell.

9. The cardiac assist device of claim 1 wherein the shell further includes apertures in the outer wall thereof for each compartment, each aperture being adapted for connection to a fluid line for providing communication between one of the compartments and a fluid pump.

10. The cardiac assist device of claim 1 wherein the shell has a substantially semi-spherical shape.

11. A method of securing a cardiac assist device to a heart, the device including a flexible, nondistensible shell having inner and outer walls, an open upper end, and a plurality of inflatable compartments within the shell, the method comprising:
    positioning the shell over the base of the heart;
    securing a band substantially 360° around the aorta; and
    connecting a first strap to the band and to the shell to hold the shell in position on the heart.

12. The method of claim 11 the first strap extends behind the left atrium and between the heart and transverse sinus.

13. The method of claim 12 further comprising connecting a second strap to the band and to the shell and extending the second strap in front of the right atrium.

14. The method of claim 11 further comprising connecting a circumferential strap to the upper end of the shell so as to extend around the base of the heart.

15. The method of claim 11 wherein the shell is held in position on the heart without the use of suction or sutures.

16. A heart bag for assisting systolic contractions of the heart, comprising:
    a flexible, non-distensible shell shaped to fit around the base of the heart and having inner and outer walls;

a distensible membrane within the shell defining an inflatable space extending continuously along the inner wall of the shell;

a plurality of inflatable chambers positioned interiorly of the inflatable space for engaging the ventricles of the heart; and a plurality of straps connected to the shell and extending around the heart for holding the bag in position on the heart.

17. The heart bag of claim 16 wherein the shell includes an aperture therein for providing fluid communication to the inflatable space.

18. The heart bag of claim 16 wherein the straps are adjustable.

19. The heart bag of claim 16 wherein the plurality of straps includes a first strap adapted to extend around the aorta and a second strap adapted to extend around the base of the heart.

20. The heart bag of claim 16 wherein the plurality of chambers includes a first chamber for engaging the left ventricle and second and third chambers for engaging the right ventricle.

21. The heart bag of claim 16 wherein the shell includes an aperture extending therethrough to provide fluid communication from a fluid source to each chamber.

* * * * *